US008100909B2

(12) United States Patent
Butler et al.

(10) Patent No.: US 8,100,909 B2
(45) Date of Patent: Jan. 24, 2012

(54) SELF-CONTAINED ASSEMBLY FOR INSTALLATION OF ORTHOPEDIC IMPLANT COMPONENTS ONTO AN ORTHOPEDIC IMPLANT

(75) Inventors: Michael S. Butler, St. Charles, IL (US); Daniel Predick, Chicago, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 455 days.

(21) Appl. No.: 12/412,701

(22) Filed: Mar. 27, 2009

(65) Prior Publication Data

US 2009/0248030 A1 Oct. 1, 2009

Related U.S. Application Data

(60) Provisional application No. 61/072,070, filed on Mar. 27, 2008.

(51) Int. Cl.
*A61B 17/00* (2006.01)
(52) U.S. Cl. .......................................... 606/60; 606/151
(58) Field of Classification Search .................... 606/99, 606/104, 101; 623/17.11
See application file for complete search history.

(56) References Cited

U.S. PATENT DOCUMENTS

| 4,946,458 A | 8/1990 | Harms et al. | |
|---|---|---|---|
| 5,941,885 A | 8/1999 | Jackson | |
| 2004/0039383 A1 | 2/2004 | Jackson | |
| 2008/0077139 A1* | 3/2008 | Landry et al. | 606/61 |
| 2009/0005787 A1* | 1/2009 | Crall et al. | 606/104 |
| 2009/0248089 A1* | 10/2009 | Jacofsky et al. | 606/311 |
| 2009/0254125 A1* | 10/2009 | Predick | 606/264 |
| 2009/0281579 A1* | 11/2009 | Weaver et al. | 606/286 |
| 2010/0057136 A1* | 3/2010 | Heiges et al. | 606/301 |
| 2010/0094349 A1* | 4/2010 | Hammer et al. | 606/264 |
| 2010/0168796 A1* | 7/2010 | Eliasen et al. | 606/264 |
| 2010/0198272 A1* | 8/2010 | Keyer et al. | 606/302 |
| 2010/0204735 A1* | 8/2010 | Gephart et al. | 606/264 |

* cited by examiner

*Primary Examiner* — Suzette J Gherbi
(74) *Attorney, Agent, or Firm* — Foley & Lardner LLP

(57) ABSTRACT

A self-contained orthopedic implant component assembly provides for concerted or concerted and independent installation of orthopedic components onto an orthopedic implant. The assembly includes a first orthopedic component formation for installation of a first orthopedic component thereof onto the orthopedic implant and a second orthopedic component formation for installation of a second orthopedic component thereof onto the orthopedic implant. The second orthopedic implant formation is carried by the first orthopedic implant formation such that installation of the first orthopedic implant formation into the orthopedic implant at least partially installs the second orthopedic implant formation into the orthopedic implant. One or both of the first and second orthopedic component formations includes a component driver for receipt of installation torque whereby application of rotational torque installs the orthopedic component(s) onto the orthopedic implant. A component driver is detachable from its formation during or after installation of the corresponding orthopedic component depending on form of the self-contained orthopedic implant component assembly.

19 Claims, 12 Drawing Sheets

SELF-CONTAINED ASSEMBLY FOR INSTALLATION OF ORTHOPEDIC IMPLANT COMPONENTS ONTO AN ORTHOPEDIC IMPLANT

This patent application claims the benefit of and/or priority to U.S. Provisional Patent Application Ser. No. 61/072,070 filed Mar. 27, 2008, entitled "Two-Part Assembly For Concerted Installation Of Orthopedic Implant Components Onto An Orthopedic Implant" the entire contents of which is specifically incorporated herein by this reference.

BACKGROUND OF THE INVENTION

1. Field of the Invention

The present invention relates to orthopedic implants such as spine fixation components, constructs and assemblies and, more particularly, to installation components for such orthopedic implants.

2. Background Information

Orthopedic implants have made a profound contribution to the correction of orthopedic deformities, accidents and other problems. During orthopedic surgery, it is often necessary to install certain orthopedic implants in several steps. One or more of these steps may require that various implant components be added to or installed in the overall orthopedic implant. However, the more steps and implant components that need to be added to or installed in the overall orthopedic implant, the more likely that assembly problems such as misalignment or the like are encountered.

In the area of the orthopedic correction of spinal deformities, accidents and other problems, orthopedic implants such as spine plates, spinal bone screw assemblies for spinal rods and other devices (spinal components) are used for spine problems in the cervical, thoracic, lumbar and sacral spine. These and other spinal devices are typically fixed to vertebrae using vertebral bone screws. Vertebral bone screws are specially designed and manufactured bone screws that are placed into the bone of a vertebra. One typical placement of a bone screw for the fixation of a spinal component is through a pedicle of the vertebral body. Vertebral bone screws placed in this manner offer superior strength and pull-out resistance as compared to other forms of fixation in spine surgery. The ability to achieve pedicle fixation has allowed surgeons to obtain more secure fixation of the involved vertebral segments, which permits more powerful correction of spine problems and reported better clinical outcomes. Vertebral bone screws for pedicle fixation may be known as pedicle screws.

Pedicle screws provide a solid foundation for the attachment of spinal rods. Spinal rods are used for the fixation of a plurality of vertebrae in order to provide orthopedic solutions for various spinal problems. A spinal rod is held relative to a pedicle screw by a spinal rod connector or connector assembly that is pivotally coupled to the pedicle screw. The spinal rod is locked to the spinal rod connector assembly in the last step of several separate steps of the installation process. With the number of separate steps, it is oftentimes difficult to correctly align the spinal rod connector assembly while trying to lock up the spinal rod. Correct alignment is necessary for the proper therapeutic benefit of spinal rod usage.

In view of the above, it is desirable to reduce or consolidate the number of steps involved in installing an orthopedic implant.

With regard to orthopedic spinal implants, it is particularly desirable in the case of spinal rod fixation components to reduce or consolidate the number of steps involved in locking up a spinal rod in a spinal rod connector assembly.

SUMMARY OF THE INVENTION

A self-contained orthopedic implant component assembly provides for concerted installation of orthopedic components onto an orthopedic implant. The assembly includes a first orthopedic component formation for installation of a first orthopedic component thereof onto the orthopedic implant and a second orthopedic component formation for installation of a second orthopedic component thereof onto the orthopedic implant. The second orthopedic implant formation is carried by the first orthopedic implant formation such that installation of the first orthopedic implant formation into the orthopedic implant at least partially installs the second orthopedic implant formation into the orthopedic implant.

One or both of the first and second orthopedic component formations includes a component driver for receipt of installation torque whereby application of rotational torque installs the orthopedic component(s) onto the orthopedic implant. A component driver is detachable from its formation during or after installation of the corresponding orthopedic component depending on the form of the self-contained orthopedic implant component assembly.

In one form, the self-contained orthopedic implant component assembly is a two-part spinal implant component assembly having a first combined spinal component and spinal component driver formation, and a second combined spinal component and spinal component driver formation. The first and second combined spinal component and spinal component driver formations are situated relative to one another to provide independent and concerted installation of the first and second spinal components thereof onto a spinal implant.

The first component and component driver formation may be formed by two, detachable portions that are separated from one another after installation of the first component. Likewise, the second component and component driver formation may be formed by two, detachable portions that are separated from one another after installation of the second component.

In one form thereof, the two-part spinal implant component assembly comprises a combined spinal rod holder end cap and spinal rod holder end cap driver, and a combined spinal rod set screw and spinal rod set screw driver, particularly for a spinal rod holder of a spinal rod bone screw assembly, that provides independent but concerted installation of the spinal rod holder end cap of the combined spinal rod holder end cap and spinal rod holder end cap driver along with the spinal rod set screw of the combined spinal rod set screw and spinal rod set screw driver onto and/or into the spinal rod holder. Rotational movement of the combined spinal rod holder end cap and spinal rod holder end cap driver with the combined spinal rod set screw and spinal rod set screw driver installs the spinal rod holder end cap into the spinal rod holder along with the spinal rod set screw. Independent rotation of the combined spinal rod set screw and spinal rod set screw driver fixes the spinal rod set screw relative to the spinal rod holder end cap and onto a spinal rod.

Thereafter, the spinal rod holder end cap driver is detached from the spinal rod holder end cap and removed. The spinal rod set screw driver is also detached from the spinal rod set screw and removed. Detachment is accomplished by breaking or snapping off the driver portion from the component portion. A method is also provided for independently but concertedly installing two-part orthopedic components onto/into an orthopedic implant.

In another form, the self-contained orthopedic implant component assembly is a two-part spinal implant component assembly operatively coupled to one another by a driving pin that keys the two spinal implant component assemblies together. The coupled two-part orthopedic implant component assembly has a first combined spinal component and spinal component driver formation, and a second combined spinal component and spinal component driver formation that, along with the driving pin, provides concerted installation of the first spinal implement component and the second spinal implement component, and then the independent installation of the second spinal implement component. The first and second combined spinal component and spinal component driver formations are situated relative to one another to provide concerted installation of the first and second spinal components thereof onto a spinal implant with torque applied only to the first component driver.

The first component and component driver formation may be formed by two, detachable portions that are separated from one another after installation of the first component. Likewise, the second component and component driver formation may be formed by two, detachable portions that are separated from one another after installation of the second component. In this embodiment, the first component driver detaches first, while continued rotation thereof rotates the second component driver (since it is coupled to the first component driver by the driving pin) to install the second component. Once the second component is installed, the second component driver detaches therefrom. A method is also provided for concertedly installing two-part orthopedic components onto an orthopedic implant.

In one manner, the second implant formation is installed within a bore of the first implant formation, and cross pinned through a slot by means of the transverse driving pin. The first implant is comprised of the spinal implant component as well as the only spinal component driver formation, which is then loaded into the orthopedic implant. As torque is applied to the first implant formation in the orthopedic implant, the spinal implant component is detached from the spinal component driver at a predetermined (or pre-designated) level or amount of torque (or torque value), however, the spinal component driver remains fixed to the second implant formation by means of the transverse driving pin. Torque continues to be applied to the spinal component driver of the first implant formation which then rotates the transverse driving pin (now that the first spinal implant component is detached) forcing the second implant formation to rotate and be driven axially downward by means of the internal threading. The second implant formation (spinal rod set screw) continues to be driven down until it impacts the spinal rod and is detached from the Self Contained Breakaway Assembly at its predesignated torque value.

In one form thereof, the coupled, two-part spinal implant component assembly comprises a combined spinal rod holder end cap and spinal rod holder end cap driver, and a combined spinal rod set screw and spinal rod set screw driver, particularly for a spinal rod holder of a spinal rod bone screw assembly, that provides concerted installation of the spinal rod holder end cap of the combined spinal rod holder end cap and spinal rod holder end cap driver along with the spinal rod set screw of the combined spinal rod set screw and spinal rod set screw driver onto the spinal rod holder.

The present self-contained orthopedic implant component assembly may take various forms for various applications as well as various dimensions. Moreover, the present self-contained orthopedic implant component assembly may be embodied in an implant other than for the spine.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

Figure 1:
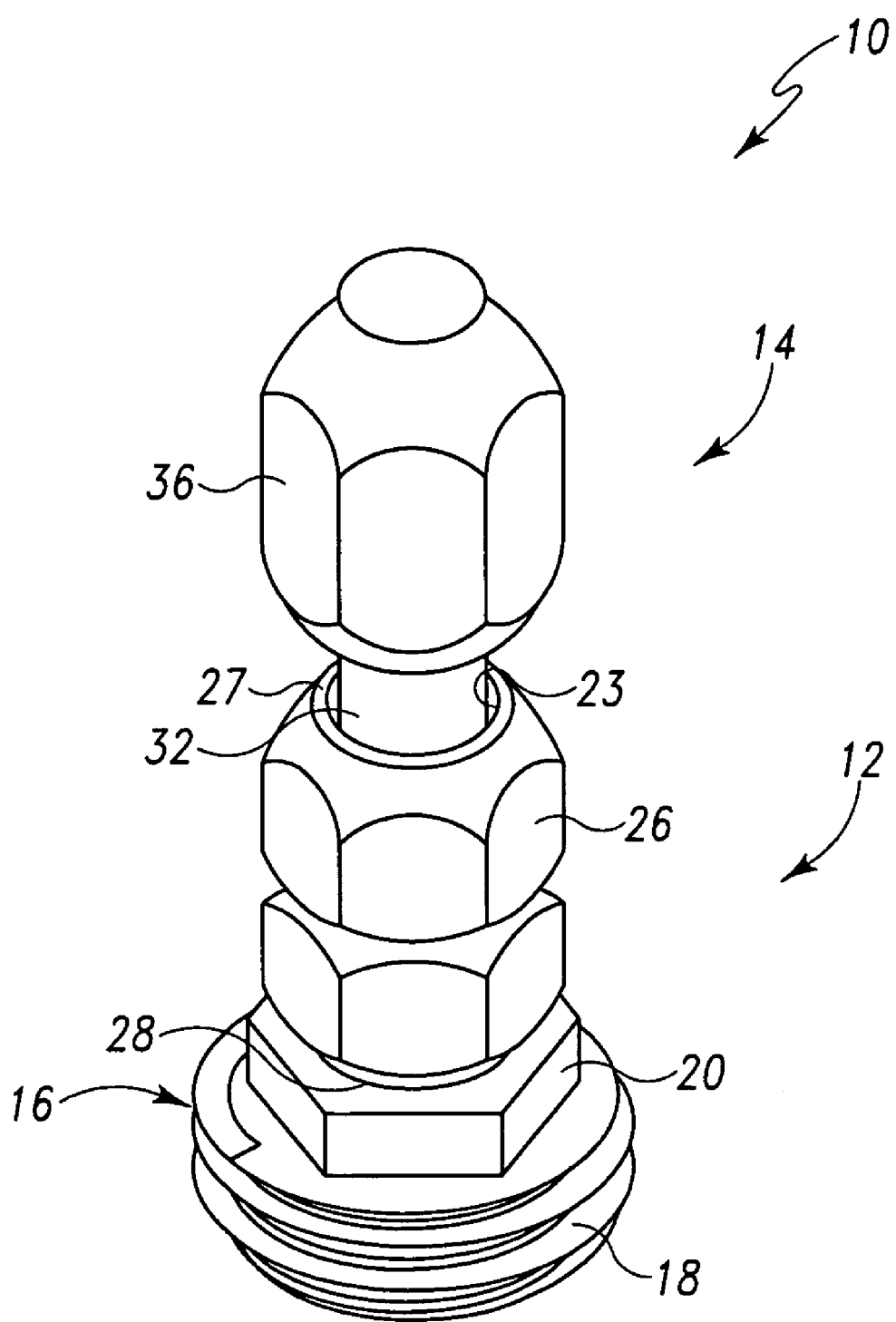
FIG. 1 is a perspective view of a self-contained orthopedic implant component assembly for installing orthopedic implant components onto an orthopedic implant, the self-contained orthopedic implant component assembly embodied as a spinal implant component assembly for installing spinal implant components onto a spinal implant, and particularly for installing a spinal rod holder end cap and spinal rod set screw onto a spinal rod holder assembly.
Figure 2:
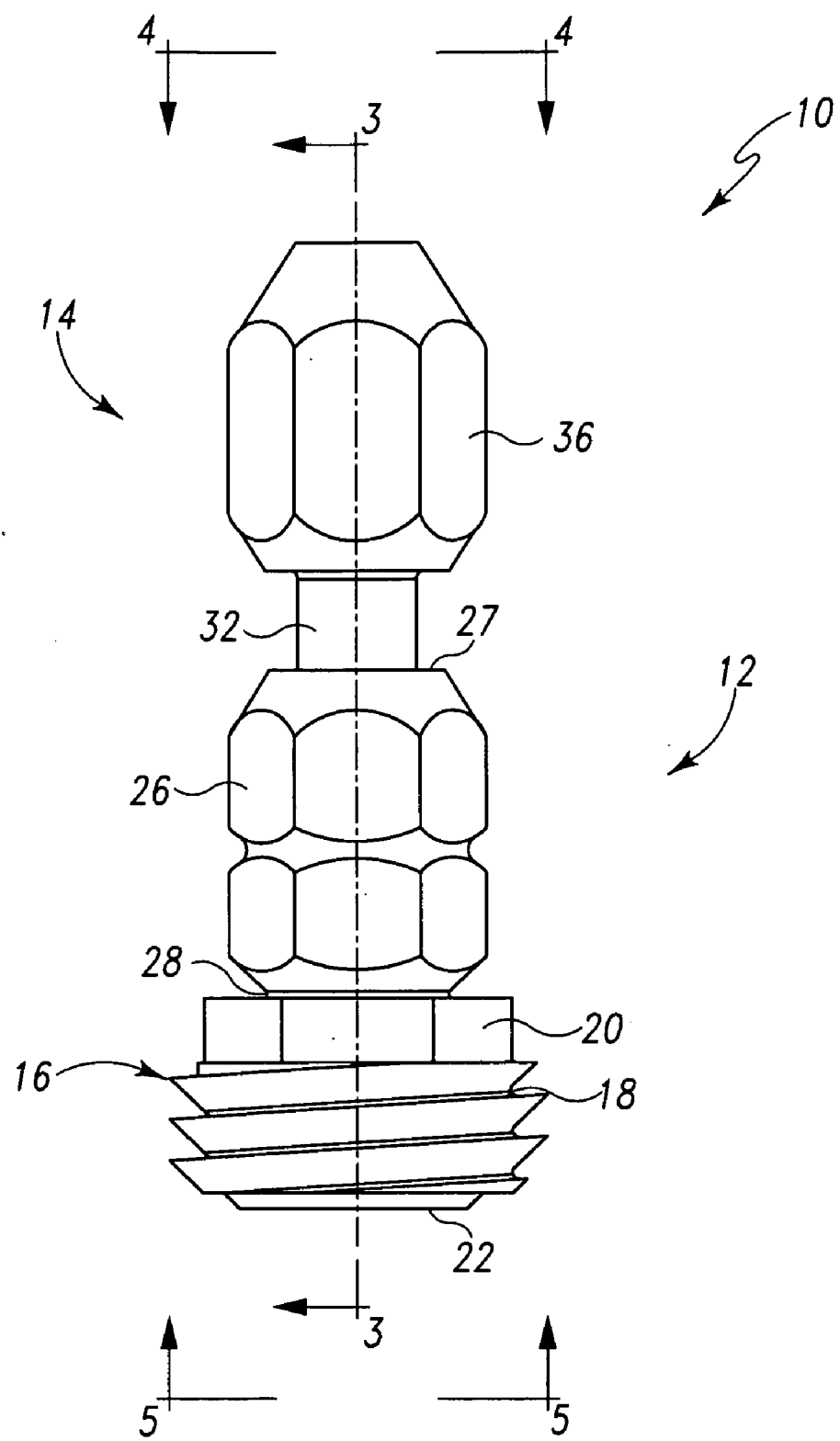
FIG. 2 is a front plan view of the self-contained spinal implant component assembly of FIG. 1.

A description of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF EMBODIMENTS OF THE INVENTION

FIGS. 1-5 depict various views of an exemplary self-contained orthopedic implant component assembly fashioned in accordance with the present principles. The self-contained orthopedic implant component assembly is embodied in FIGS. 1-5 as a two-part self-contained orthopedic implant component assembly and includes first and second component and component driver formations 12, 14. The first and second component and component driver formations 12,14 are configured for independent and/or concerted installation of the first and second components thereof into and/or onto an orthopedic implant and for the removal of the first and second component drivers thereof from the first and second components. Each one of the first and second component and component driver formations is formed by two, detachable portions that are separable from one another after installation of the corresponding component.

The two-part orthopedic implant component assembly as embodied in FIGS. 1-5 has a first combined spinal component and spinal component driver formation, and a second combined spinal component and spinal component driver formation. The first and second combined spinal component and spinal component driver formations are situated relative to one another to provide independent but concerted installation of the first and second spinal components thereof onto and/or into a spinal implant. The two-part spinal implant component assembly 10 comprises a combined spinal rod holder end cap and spinal rod holder end cap driver 12, and a combined spinal rod set screw and spinal rod set screw driver 14, particularly for a spinal rod holder of a spinal rod bone screw assembly (see spinal rod bone screw assembly 50 of FIGS. 6 and 7), that provides independent but concerted installation of the spinal rod holder end cap along with the spinal rod set screw onto and/or into the spinal rod holder.

Particularly, the two-part orthopedic implant component assembly 10 is used for concertedly installing an end cap 16 and a spinal rod set screw 30 into a spinal rod connector head or holder 60 (of the spinal rod connector assembly 50 of FIGS. 6 and 7) and locking up a spinal rod (see, e.g., spinal rod 80 of FIGS. 6 and 7) in the spinal rod connector assembly of a pedicle screw assembly (see, e.g. pedicle screw assembly 50 of FIGS. 6 and 7) independent of the setting of the end cap. The various components of the present two-part orthopedic implant component assembly 10 are made from a bio-compatible material such as stainless steel or titanium. Other bio-compatible materials, of course, may be used.

The two-part orthopedic implant component assembly 10 consists of a first part end cap assembly 12 (end cap assembly 12) and a second part spinal rod set screw assembly 14 (spinal rod set screw assembly 14). The end cap assembly 12 receives the spinal rod set screw assembly 14 both of which are installable or implantable into a spinal rod connector assembly in a concerted manner while allowing for independent fixation of a portion of the end cap assembly 12 relative to the fixation of a portion of the spinal rod set screw assembly 14.

The end cap assembly is characterized by a body defining an end cap 16 and a collar 26 forming a component (end cap) driver. The end cap 16 is generally annular in shape and has external threads 18 thereon. The end cap 16 includes a hex portion 20 axially above the threads 18 that is sized to receive a hex driver of a first size. The collar 26 is configured as a hex shape in like manner as the hex portion 20 of the end cap 16 but of a smaller size than that of the hex portion 20. The collar 26 also receives a hex driver but of a second size that is smaller than the hex driver for the hex portion 20.

Figure 3:
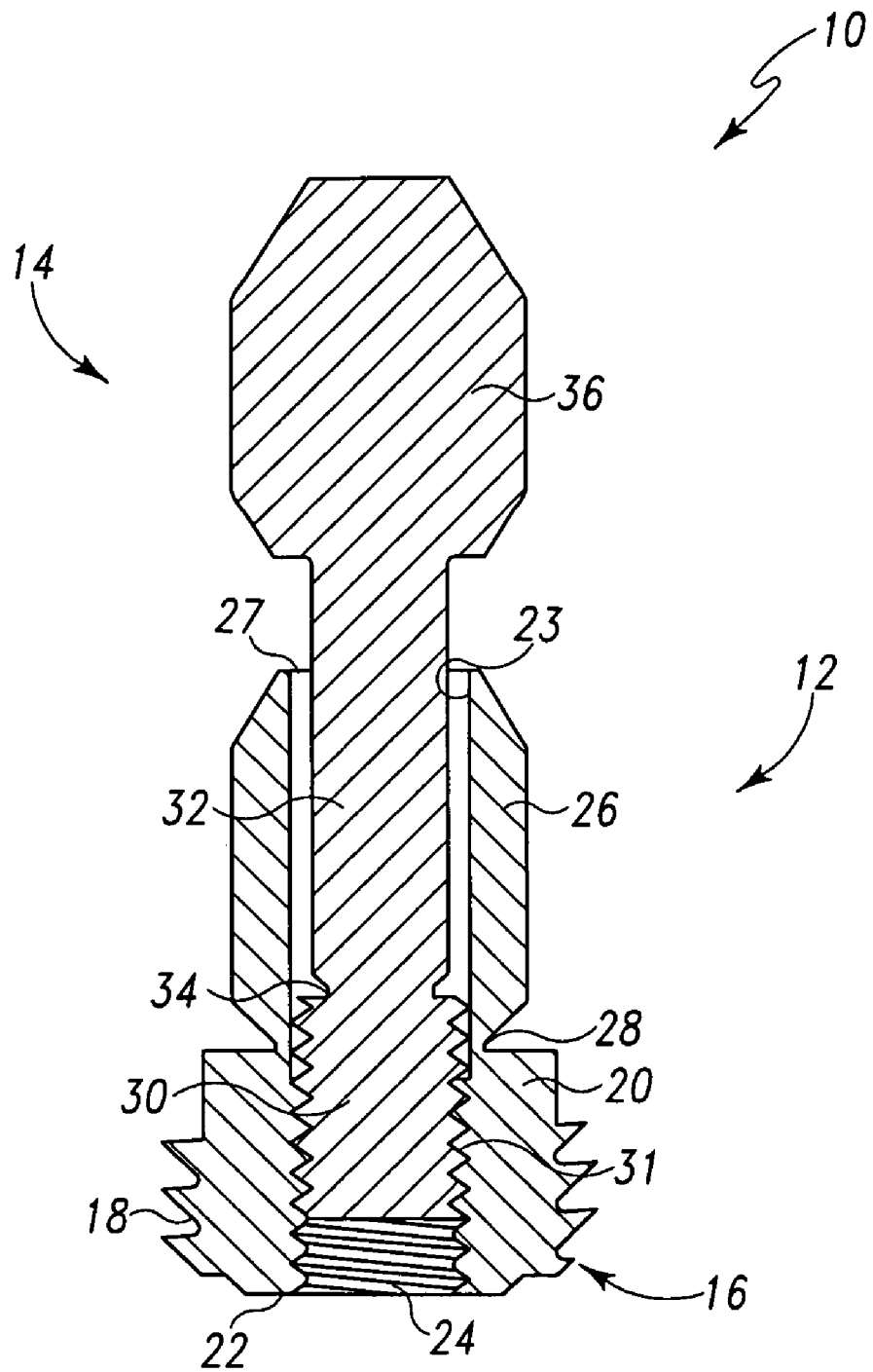
FIG. 3 is a sectional view of the self-contained spinal implant component assembly of FIG. 1 taken along line 3-3 of FIG. 2.
Figure 4:
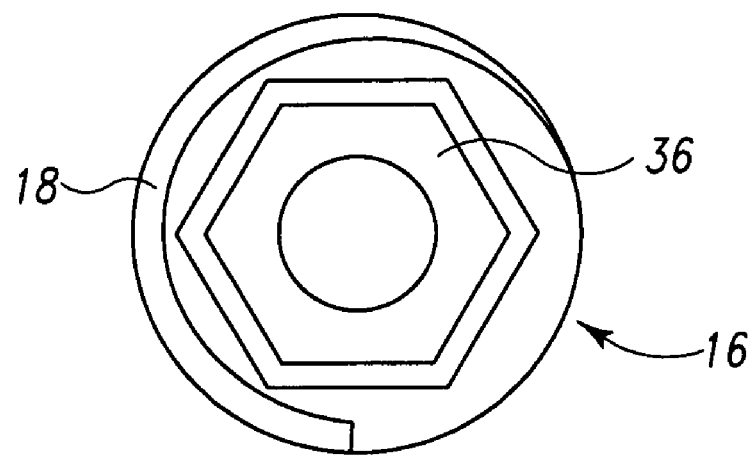
FIG. 4 is a top plan view of the self-contained spinal implant component assembly of FIG. 1 taken along line 4-4 of FIG. 2.
Figure 5:
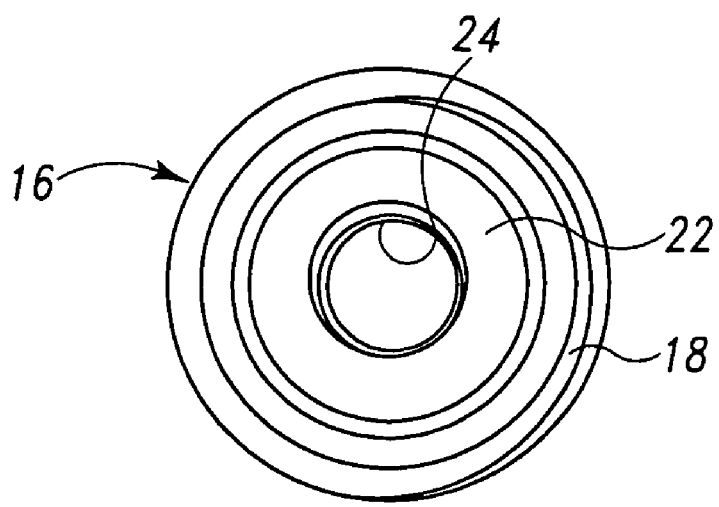
FIG. 5 is a bottom plan view of the self-contained spinal implant component assembly of FIG. 1 taken along line 3-3 of FIG. 2.

As best seen in FIG. 3, the end cap assembly 12 also has a bore 23 that extends axially through the end cap assembly 12 and particularly extends from an end 27 of the collar 26 to an end 22 of the end cap 16. The bore 23 includes a threaded portion 24 that axially extends a distance from the end 22 towards the collar 26.

In accordance with an aspect of the present invention, a junction or juncture 28 between the collar 26 and the hex portion 20 of the end cap 16 of the end cap assembly 12 is reduced in thickness between the inner and outer surface thereof or scored relative to the collar 16 and the hex portion 20. This allows the collar 26 to be snapped off, broken away or removed from the end cap 16 so as to allow the end cap 16 to remain. The collar 26 thus is and forms a detachable portion of the end cap assembly 12.

The spinal rod set screw assembly 14 is characterized by a body defining a generally cylindrical shaft 32 having a set screw or set screw portion 30 on one axial end thereof and an elongated hex head 36 on another axial end thereof. The elongated hex head 36 is sized to that of the collar 36 such that the same sized hex driver can concertedly drive the spinal rod set screw assembly 14 and the end cap assembly 12. The set screw 30 has external threads 31 on an axial length thereof that are sized to be threadedly received by the internal threads 24 of the axial bore 23 of the end cap assembly 12. Thus, the spinal rod set screw assembly 14 is threadedly received in and by the end cap assembly 12 by threaded reception of the set screw 30 in the bore 23.

In accordance with an aspect of the present invention, a junction or juncture 34 between the shaft 32 and the set screw 30 of the spinal rod set screw assembly 14 is reduced in diameter or is scored. This allows the shaft 32 and the elongated hex head 36 to be snapped off, broken away or removed from the set screw 30 so as to allow the set screw 30 to remain. The shaft 32 and the elongated hex head 36 thus is and forms a detachable portion of the spinal rod set screw assembly 14.

Because the junction 34 of the spinal rod set screw assembly 14 and the junction 28 of the end cap assembly 12 are essentially situated radially of one another, the force or bias from the second hex driver removes both the detachable portion of the end cap assembly 12 and the detachable portion of the spinal rod set screw assembly 14. As described below in greater detail, installation of the two-part orthopedic implant component assembly 10 in one form results in the breakage of the detachable portion of the end cap assembly 12 before the breakage of the detachable portion of the spinal rod set screw assembly 14. In this form, the end cap assembly 12 "bottoms out" before the spinal rod set screw assembly "bottoms out." In another form, installation of the two-part orthopedic implant component assembly 10 results in the breakage of the detachable portion of the end cap assembly 12 and the breakage of the detachable portion of the spinal rod set screw assembly 14 at the same time (simultaneously). In this form, the end cap assembly 12 "bottoms out" at the same time that the spinal rod set screw assembly "bottoms out." In yet another form, installation of the two-part orthopedic implant component assembly 10 results in the breakage of the detachable portion of the end cap assembly 12 and the breakage of the detachable portion of the spinal rod set screw assembly 14 at virtually or close to the same time (near simultaneously). In this form, the end cap assembly 12 "bottoms out" just before the spinal rod set screw assembly "bottoms out."

Figure 6:
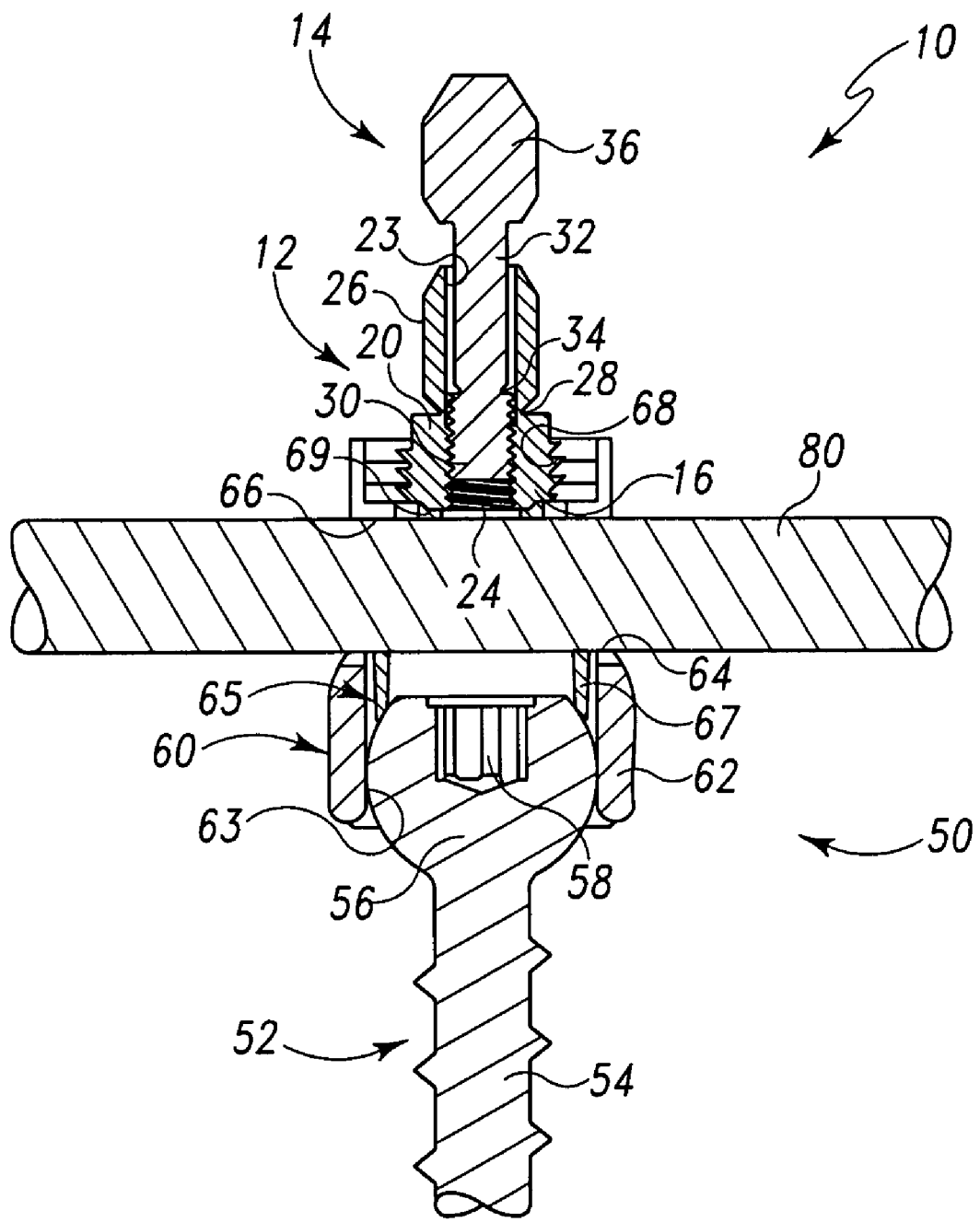
FIG. 6 is a sectional view of a spinal rod holder or vertebral bone screw assembly having a spinal rod holder with a spinal rod therein, the self-contained spinal implant component assembly of FIG. 1 situated thereon and ready to fix the spinal rod into the spinal rod holder with its spinal rod end cap and spinal rod set screw.
Figure 7:
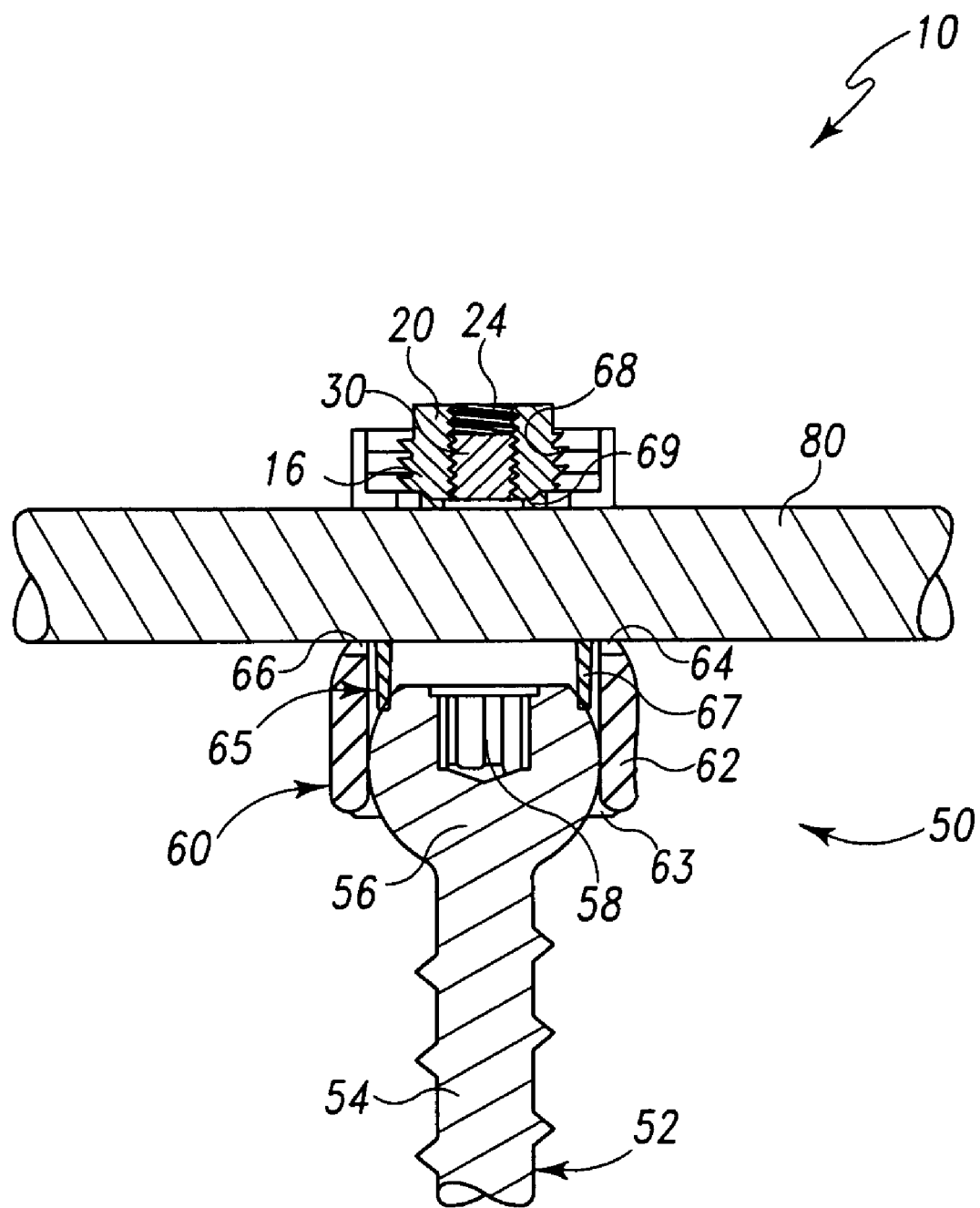
FIG. 7 is the sectional view of the spinal rod holder assembly having a spinal rod holder with a spinal rod therein of FIG. 6 with the spinal rod holder end cap and the spinal rod set screw installed therein, the spinal rod holder end cap driver and the spinal rod set screw driver (detachable portions) having been removed therefrom.
Figure 8:
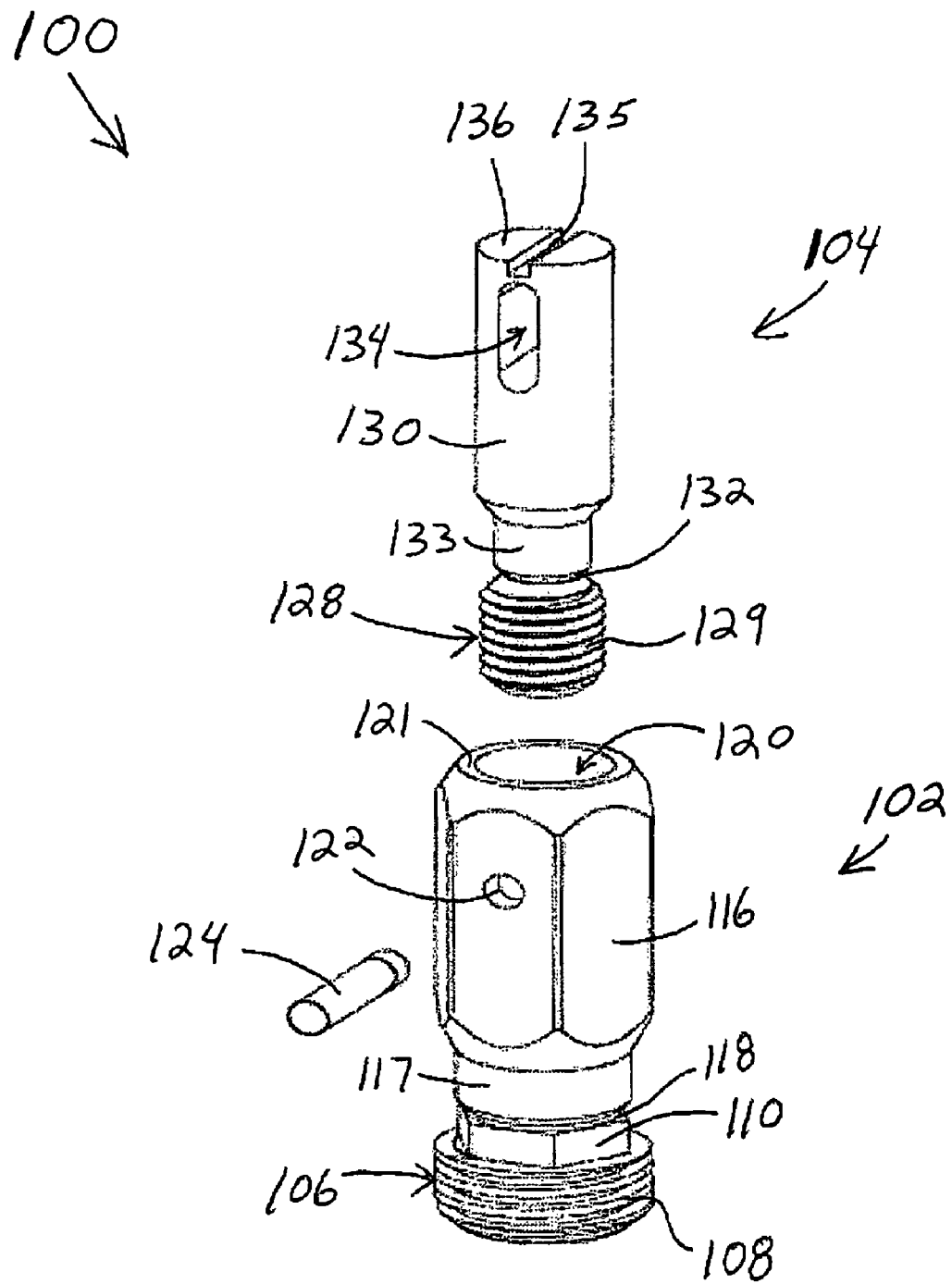
FIG. 8 is an exploded perspective view of another self-contained orthopedic implant component assembly for installing orthopedic implant components onto an orthopedic implant, the self-contained orthopedic implant component assembly embodied as another spinal implant component assembly for installing spinal implant components onto a spinal implant, and particularly for installing a spinal rod holder end cap and spinal rod set screw onto a spinal rod holder assembly.
Figure 11:
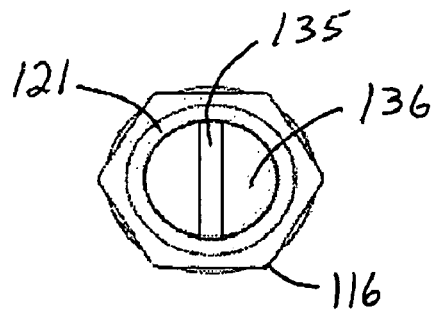
FIG. 11 is a top plan view of the self-contained spinal implant component assembly of FIG. 8 taken along line 11-11 of FIG. 9.
Figure 9:
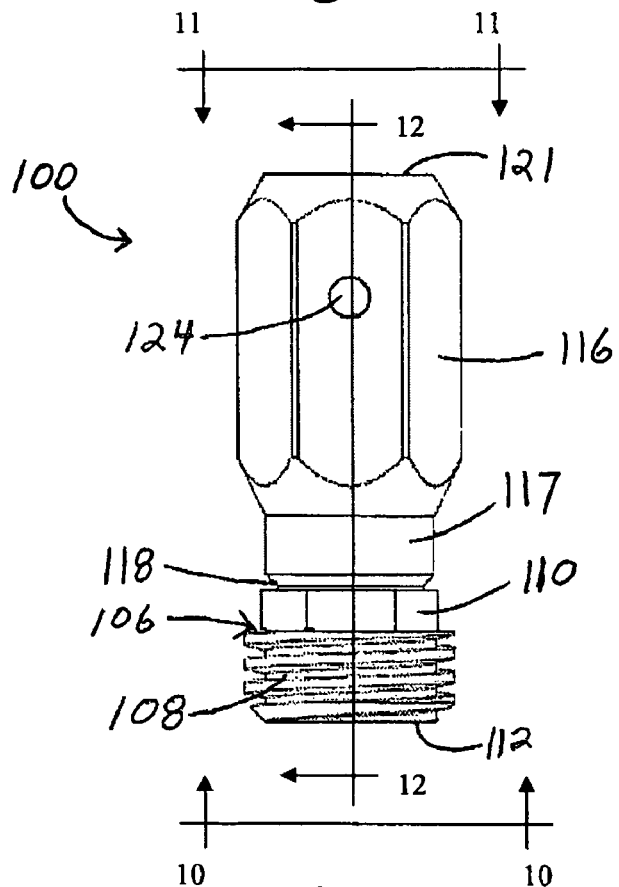
FIG. 9 is a front plan view of the assembled self-contained spinal implant component assembly of FIG. 8.
Figure 10:
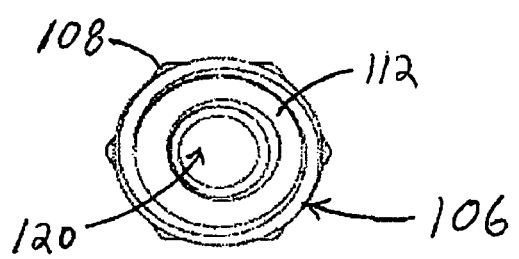
FIG. 10 is a bottom plan view of the self-contained spinal implant component assembly of FIG. 8 taken along line 10-10 of FIG. 9.

FIGS. 6 and 7 depict a manner of use of the present two-part orthopedic implant component assembly 10. FIGS. 6 and 7 depict a pedicle screw assembly 50 comprised of a pedicle screw 52 and a spinal rod connector assembly 60. The pedicle screw 52 is characterized by an externally threaded shaft or shank 54 (of which a lower portion is not shown in FIGS. 6 and 7) and a rounded head 56 having a configured socket 58. The spinal rod connector assembly 60 is characterized by a "tulip head" 62 having a lower opening 63 sized to allow the shaft 54 of the pedicle screw 52 to extend therethough but to rotatably capture the head 58 of the pedicle screw 52. The tulip head 62 has first and second openings 64 and 66 through which a spinal rod 80 extends (of which only a portion is shown in the figures). The tulip head 62 further has a threaded upper opening 68 that is sized to receive the end cap 16 of the two-part orthopedic implant component assembly 10 (and particularly of the end cap assembly 12 thereof).

It should be appreciated that the present invention may be and is contemplated for use in other types of implants or orthopedic implants including spinal rod fixation assemblies of types other than the tulip head design shown in FIGS. 6 and 7 (collectively, implant devices) that require multi-torque settings and/or to lock up implant devices requiring two settings to lock in one step. Moreover, the principles of the present invention apply to orthopedic implant components that provide more than the installation of two components.

As shown in FIG. 6, the end cap assembly 12 with the spinal rod set screw assembly 14 is threadedly received in the threaded upper opening 68 of the tulip head 62 via a hex driver of appropriate size (not shown) that receives the hex portion 20 of the end cap assembly 12 and the hex head 26 of the spinal rod set screw assembly 14. The spinal rod set screw assembly 14 is thus first threaded into the end cap assembly 12 for a particular distance. Via the hex driver, the set screw assembly 14 and the end cap assembly 12 are simultaneously driven downwardly or situated in or on the tulip head 62. As the hex driver simultaneously drives the end cap assembly 12 and the spinal rod set screw assembly 14 into the tulip head 62, the end cap 16 abuts, contacts or bottoms out onto the upper end 69 of the taper lock 65. This compresses the lower end 67 of the taper lock 65 against an upper portion of the head 56 of the pedicle screw 52. This forces a lower part of the head 56 of the pedicle screw 52 into the tapered opening 63 of the tulip head 62 to stop rotation of the pedicle screw 52 relative to the tulip head 62 and thus fix the angular orientation of the pedicle screw 52 relative to the tulip head 62.

Referring to FIG. 7, once the end cap assembly 12 is properly situated in the tulip head 62, the torque of continued rotation of the hex driver breaks or snaps off from the hex portion 20 (the detachable portion) of the end cap assembly 12 and into the hex driver. As the hex driver continues to turn, the spinal rod set screw assembly 14 is driven downward through the end cap assembly 12 until the set screw 30 axially abuts, contacts or bottoms out (compresses) against the spinal rod 80. This forces the spinal rod 80 axially downward to compress against the openings 64, 66 of the tulip head 62 thereby fixing the spinal rod 80 against the tulip head 62. The torque breaks or snaps off the hex head 26 (detachable portion) of the spinal rod set screw assembly 14 into the hex driver. The two detachable portions remain in the hex driver to be removed therefrom. Thus, the installation of the implant components and the setting of the orientation of the spinal rod is accomplished independently but concertedly using the principles of the present invention. Removal of the remaining assembly 10 is accomplished using the hex portion 20 of the end cap 16.

FIGS. 8-13 depict various views of another exemplary self-contained orthopedic implant component assembly 100 fashioned in accordance with the present principles. The self-contained orthopedic implant component assembly is embodied in FIGS. 8-13 as a self-contained coupled orthopedic implant component assembly and includes first and second component formations 102, 104 that are coupled to one another via a driving pin 124. The first and second component formations 102,104, together with the driving pin 124, are configured for concerted installation of the first and second components thereof into and/or onto an orthopedic implant and for the removal of the first and second component drivers thereof from the first and second components after installation. Each one of the first and second component and component driver formations is formed by two, detachable portions that are separable from one another for a given amount of torque.

Particularly, the coupled spinal implant component assembly 100 comprises a combined spinal rod holder end cap and spinal rod holder end cap driver 102, and a combined spinal rod set screw and spinal rod set screw driver 104, along with driving pin 124 particularly for a spinal rod holder of a spinal rod bone screw assembly (see spinal rod bone screw assembly 150 of FIGS. 13 and 14), that provides independent but concerted installation of the spinal rod holder end cap 106 along with the spinal rod set screw 128 onto and/or into the spinal rod holder.

Particularly, the two-part orthopedic implant component assembly 100 is used for concertedly installing the end cap 106 and a spinal rod set screw 128 into a spinal rod connector head or holder 160 (of spinal rod connector assembly 160 of FIGS. 13 and 14) and then locking up a spinal rod (see the spinal rod 200 of FIGS. 13 and 14) therein by the setting of the end cap during continued rotation of the end cap driver. The various components of the present coupled orthopedic implant component assembly 100 are made from a bio-compatible material such as stainless steel or titanium. Other bio-compatible materials, of course, may be used.

The coupled orthopedic implant component assembly 100 consists of a first part end cap assembly 102 (end cap assembly 102) and a second part spinal rod set screw assembly 104 (spinal rod set screw assembly 104). The end cap assembly 102 receives the spinal rod set screw assembly 104 within a bore 120 thereof, both of which are installable or implantable into a spinal rod connector assembly in a concerted manner while allowing for independent fixation of the set screw 128. The end cap assembly 102 is characterized by a body defining an end cap 106 with a component driver 116 (i.e. an end cap driver) extending from a collar 117. The end cap 106 is generally annular in shape and has external threads 108 thereon. A hex portion 110 is disposed axially above the threads 108, and is sized to receive a hex driver of a first size. The collar 117 is axially above the hex portion 110 and is generally annular. The component driver 116 is configured as a hex shape for receiving a hex driver (not shown).

The end cap assembly 102 also has a bore 120 that extends axially through the end cap assembly 102 and particularly extends from an end or rim (top) 121 of the driver 116 to an end (bottom) 112 of the end cap 106. The bore 120 includes a threaded portion 114 that axially extends a distance from the end 112 towards the driver 116.

In accordance with an aspect of the present invention, a junction or juncture 118 between the driver 116 (collar 117) and the hex portion 110 of the end cap 106 of the end cap assembly 102 is reduced in thickness between the inner and outer surface thereof or scored relative to the driver 116 and the hex portion 110. This allows the driver 116 to be snapped off, broken away or removed from the end cap 106 so as to allow the end cap 106 to remain. The driver 116 thus is and forms a detachable portion (detachable component driver) of the end cap assembly 102.

The driver 116 has a bore 122 that extends through opposite sides of the driver 116 (of which only one side of the bore 122 in the driver 116 can be seen) that constitutes a transverse bore 122 such that the bore 122 is in communication with the axial bore 120 of the driver 116. The transverse bore 122 is sized to receive the driving or driver pin (i.e. a transverse driving pin) therein and to allow the driving pin 124 to extend through the axial bore 120 and be held by the opposite sides of the driver (see, e.g. FIG. 12). As indicated below, the driving pin is used to drive the spinal rod set screw assembly 104 in conjunction or concertedly with the driver 116. This is true when the driver 116 is attached to the end cap 106 and when the driver 116 has been detached from the end cap 106 and is still used for driving the spinal rod set screw assembly 104 for installing the set screw 128.

The spinal rod set screw assembly 104 is characterized by a body or driver defining a generally cylindrical shaft 130 having the set screw or set screw portion 128 on one axial end thereof. The shaft or driver 130 is sized for reception into the end cap assembly 102 and particularly, the bore 120 thereof. The set screw 128 has external threads 129 on an axial length thereof that are sized to be threadedly received by the internal threads 114 of the axial bore 120 of the end cap 106. Thus, the spinal rod set screw assembly 104 is threadedly received in and by the end cap assembly 102 by threaded reception of the set screw 130 in the bore 120.

Figure 12:
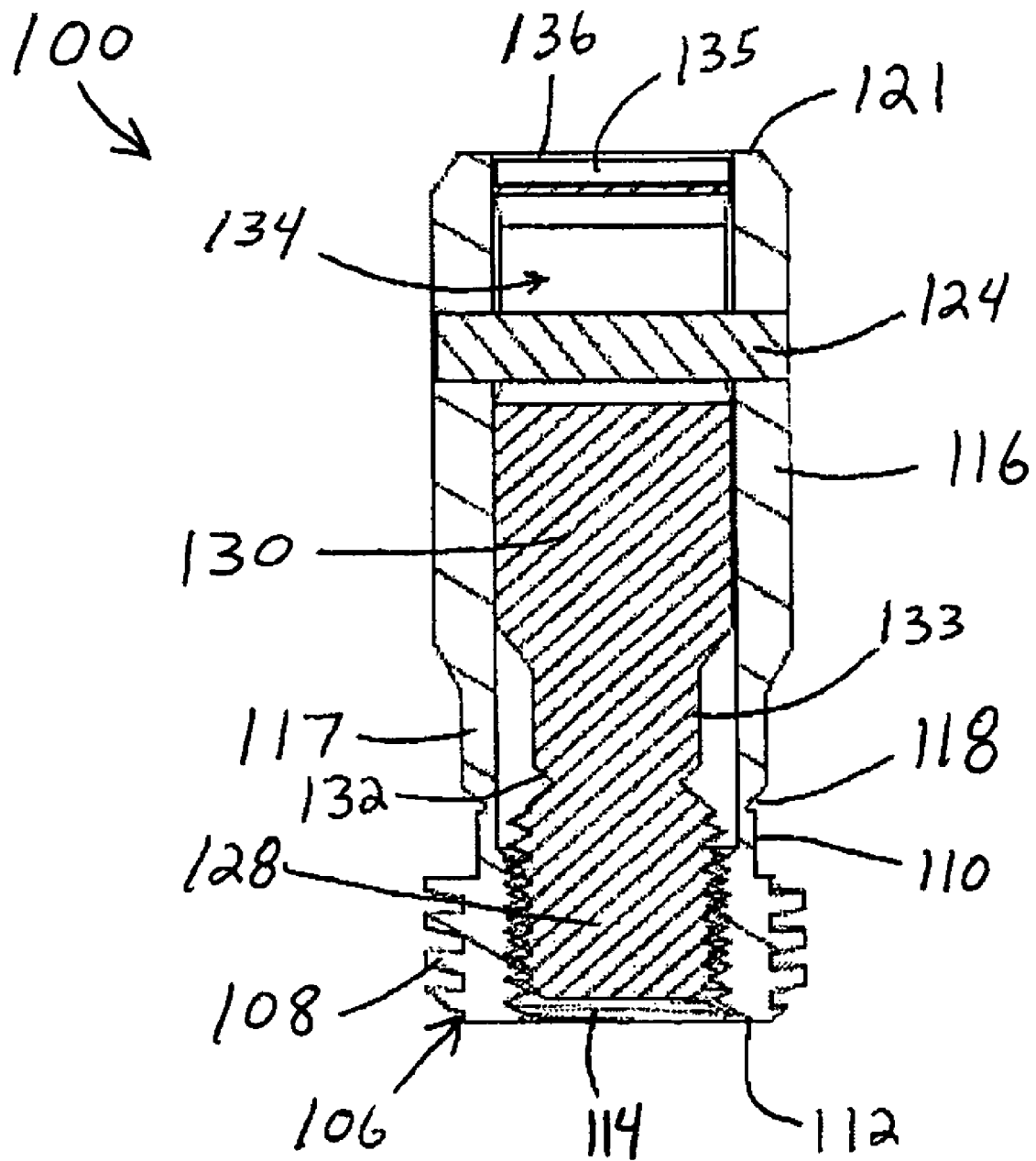
FIG. 12 is sectional view of the self-contained spinal implant component assembly of FIG. 8 taken along line 12-12 of FIG. 9.

The shaft or driver 130 has an elongated bore 134 extending therethrough from one side of the driver to the other side of the driver (see, e.g., FIG. 12). The elongated bore 134 is generally oval shaped and defines an elongated or axial cavity therein that is sized to receive the driving pin 124. The bore 134 is so sized to allow axial movement of the set screw assembly 104 within the end cap assembly 102 with the driving pin installed, thereby coupling the two assemblies 102, 104 to each other. Since the two assemblies 102, 104 are coupled to one another, rotation of the end cap assembly 102 will rotate the set screw assembly 104.

In accordance with an aspect of the present invention, a junction or juncture 132 between the shaft 130 or shaft reduction portion 133 (collectively, shaft or driver 130) and the set screw 128 of the spinal rod set screw assembly 104 is reduced in diameter or is scored or otherwise made to allow the shaft 130 to be detached therefrom. Particularly, the junction 132 allows the shaft 130 to be snapped off, broken away or removed from the set screw 128 so as to allow the set screw 128 to remain.

Figure 15:
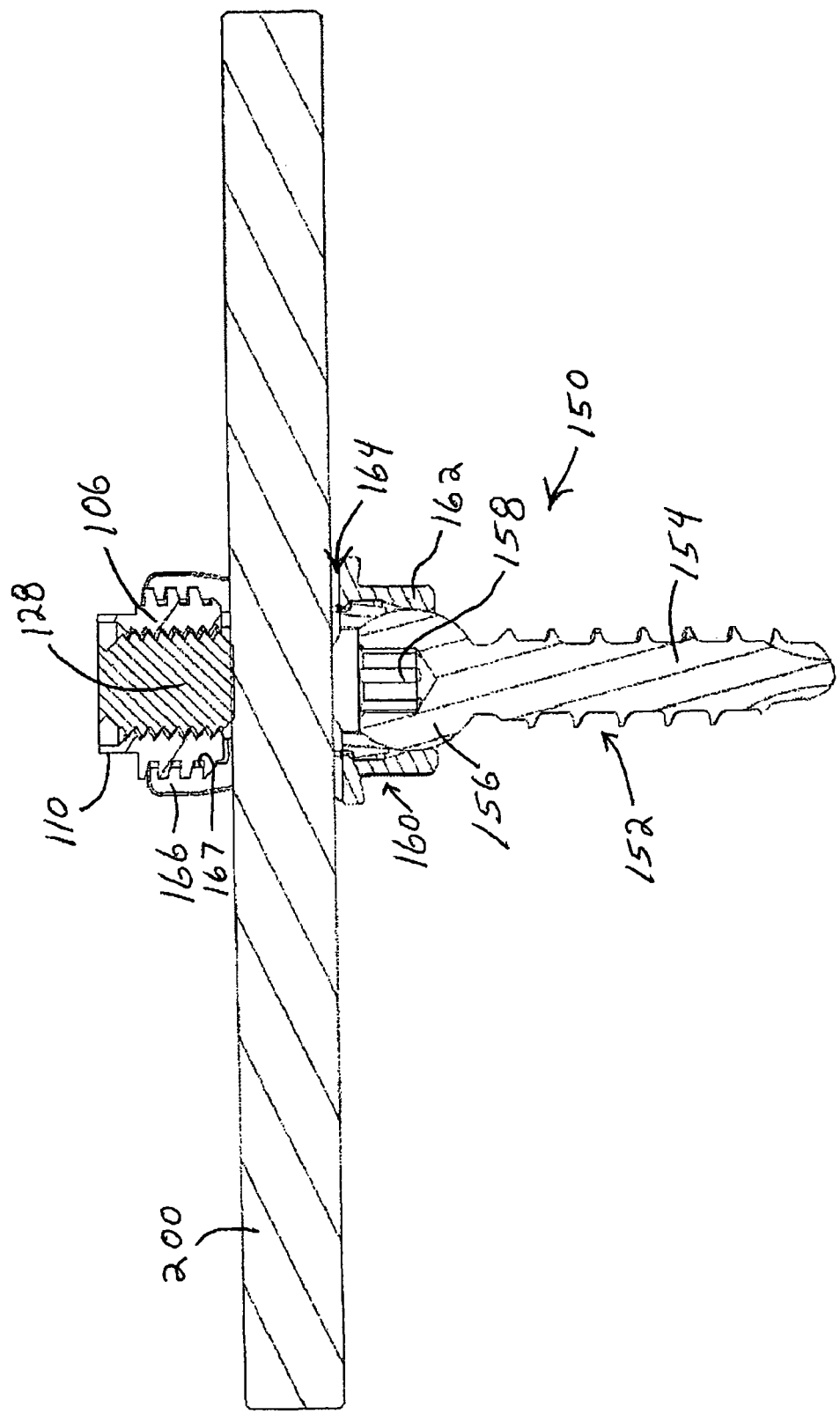
FIG. 15 is the sectional view of the another spinal rod holder assembly having a spinal rod holder with a spinal rod therein of FIG. 14 with the spinal rod holder end cap and the spinal rod set screw installed therein, the spinal rod holder end cap driver and the spinal rod set screw driver (detachable portions) having been removed therefrom.

Because the junction 132 of the spinal rod set screw assembly 104 and the junction 118 of the end cap assembly 102 are essentially situated radially of one another, and the component driver 116 of the end cap assembly 102 is coupled to the component driver 130 of the set screw assembly 104, the force or bias from a hex driver on the component driver 116 removes (detaches) both the component driver 116 from the spinal rod end cap assembly 102 and the component driver 130 from the spinal rod set screw assembly 104. Installation of the self-contained coupled orthopedic implant component assembly 100 results in the breakage of the detachable portion of the end cap assembly 102 before the breakage of the detachable portion of the spinal rod set screw assembly 104. In this form, the end cap assembly 102 "bottoms out" before the spinal rod set screw assembly 104 "bottoms out." While the detached driver 116 is freely rotatable, continued rotation of the driver 116 continues to rotate the set screw assembly 104 (the driver 130 thereof) and thus the set screw 128 thereof until the set screw 128 "bottoms out" on the spinal rod 200 (see, e.g. FIG. 15). The driver 130 detaches after bottoming out and continued torque is applied. The set screw assembly 104 axially moves relative to the driving pin 124 by virtue of the elongated slot 134 thereof. Thereafter, since the driver 130 of the set screw assembly 104 includes a slot 135 on a top 136 thereof, a slotted driver (not shown) may be used to further install (screw or thread) the set screw assembly 104 and thus the set screw 128 thereof into a final position. Moreover, since the bore 134 of the driver 130 is axially elongated, the set screw assembly 104 may be driven axially further downward relative to the end cap assembly 102.

Figure 13:
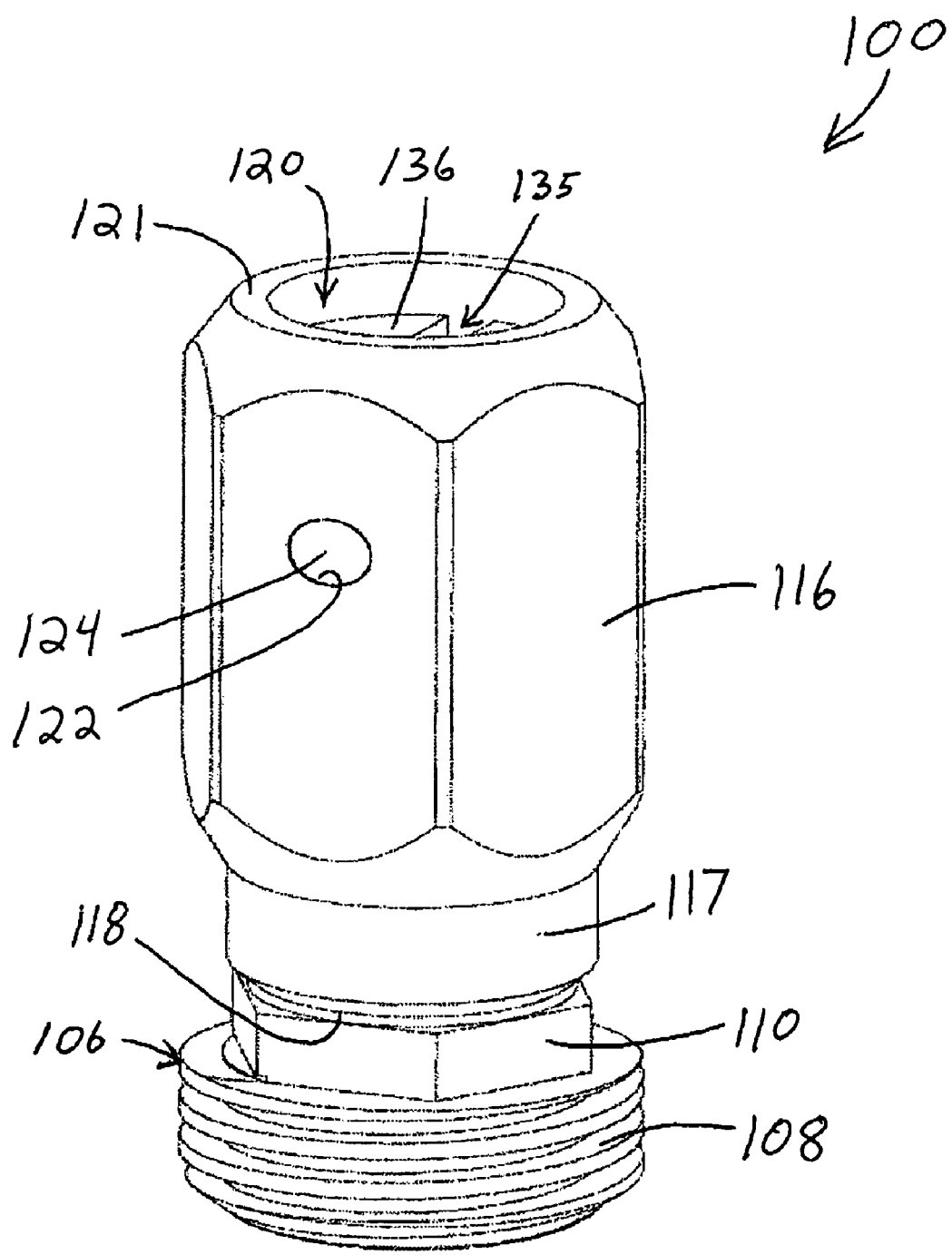
FIG. 13 is an enlarged perspective view of the assembled self-contained spinal implant component assembly of FIG. 8.
Figure 14:
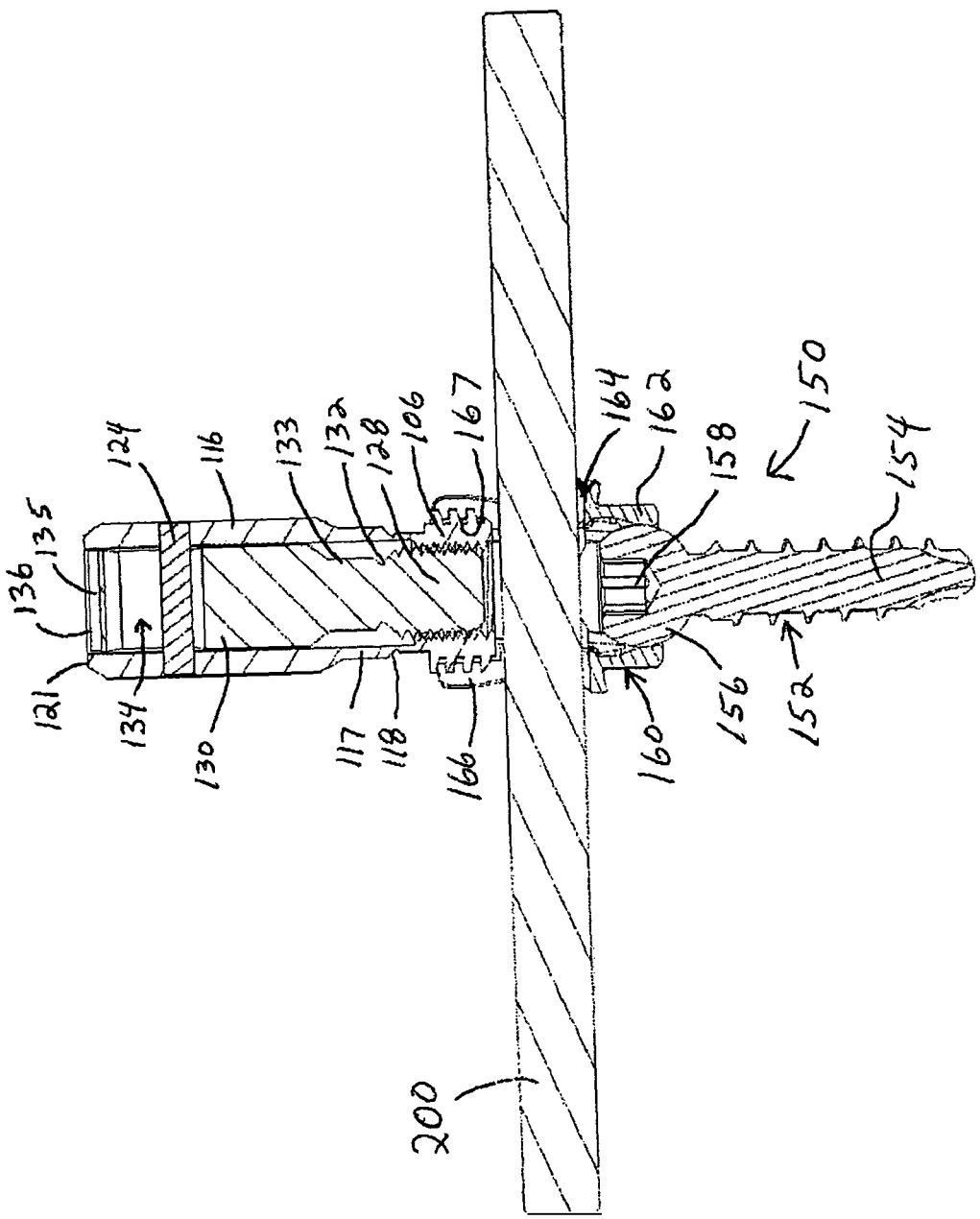
FIG. 14 is a sectional view of another spinal rod holder or vertebral bone screw assembly having a spinal rod holder with a spinal rod therein, the self-contained spinal implant component assembly of FIG. 8 situated thereon and ready to fix the spinal rod into the spinal rod holder with its spinal rod end cap and spinal rod set screw.

FIGS. 13 and 14 depict a manner of use of the present two-part orthopedic implant component assembly 100. FIGS. 13 and 14 depict a pedicle screw assembly 150 comprised of a pedicle screw 152 and a spinal rod holder 160. The pedicle screw 152 is characterized by an externally threaded shaft or shank 154 and a rounded head 156 having a configured socket 158. The spinal rod holder 160 is characterized by a lower head portion 162 having a lower opening sized to allow the shaft 154 of the pedicle screw 152 to extend there though but to rotatably capture the head 158 of the pedicle screw 152. The holder 160 has first and second openings through which a spinal rod 200 extends. The holder 160 further has an upper head portion 166 with internal threads 167 that are sized to receive the end cap 106

It should be appreciated that the present invention may be and is contemplated for use in other types of implants or orthopedic implants including spinal rod fixation assemblies of types other than the spinal rod holder/bone screw assembly design shown in FIGS. 13 and 14 (collectively, implant devices) that require multi-torque settings and/or to lock up implant devices requiring two settings to lock in one step. Moreover, the principles of the present invention apply to orthopedic implant components that provide more than the installation of two components.

As shown in FIG. 13, the end cap assembly 10 with the spinal rod set screw assembly 104 is threadedly received in the threaded upper portion 166 (opening) of the holder 160. The spinal rod set screw assembly 104 is thus first threaded into the end cap assembly 102 for a particular distance via a hex driver on the component driver 116. Via the hex driver, the end cap assembly 102 and the set screw assembly 104 are simultaneously (concertedly) driven downwardly or situated in or on the holder 160. As the hex driver simultaneously drives the end cap assembly 102 and the spinal rod set screw assembly 104 into the holder 160, the end cap 106 abuts, contacts or bottoms out within the holder 160. The angular orientation of the screw 152 is thus fixed relative to the holder 162.

Referring to FIG. 14, once the end cap 106 of the end cap assembly 102 is properly situated in the holder 160, the predetermined amount of torque of continued rotation of the hex driver breaks or snaps off the component driver 116 (the detachable portion) of the end cap assembly 10. As the hex driver continues to turn the component driver 116, the spinal rod set screw 128 of the spinal rod set screw assembly 104 is driven downward through the end cap assembly 102 until the set screw 128 axially abuts, contacts or bottoms out (compresses) against the spinal rod 200. This forces the spinal rod 200 axially downward to compress against the openings the holder 160 thereby fixing the spinal rod 200 against the holder 160. The continued torque (while the driver 116 is freely rotating having been previously detached) breaks or snaps off the component driver 130 (detachable portion) of the spinal rod set screw assembly 104 into the hex driver. The two detachable portions remain in the hex driver to be removed therefrom. Thus, the installation of the implant components and the setting of the orientation of the spinal rod is accomplished concertedly, then independently using the principles of the present invention.

It should be appreciated that the principles of the present invention may be applied to orthopedic implants devices other than pedicle screw assemblies that require installation, fixation and/or locking of two independent components.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. An apparatus for installing orthopedic implant components onto an orthopedic implant, the apparatus comprising:
    a first orthopedic implant formation defining both a first orthopedic implant component and a first orthopedic implant component driver, the first orthopedic implant component comprising an end cap for the orthopedic implant; and
    a second orthopedic implant formation defining both a second orthopedic implant component and a second orthopedic implant component driver, the second orthopedic implant component comprising a set screw for the orthopedic implant;
    the first and second orthopedic implant formations configured for at least partial concerted installation of the first orthopedic implant component and the second orthopedic implant component onto an orthopedic implant.

2. The apparatus of claim 1, wherein:
    the first orthopedic implant component comprises a first spinal implant component;
    the second orthopedic implant component comprises a second spinal implant component; and
    the orthopedic implant is a spinal implant.

3. The apparatus of claim 2, wherein:
    the spinal implant is a vertebral spinal rod bone screw assembly having a spinal rod holder.

4. The apparatus of claim 3, wherein:
    the first orthopedic implant component driver is a first hexagonal head; and
    the second orthopedic implant component driver is a second hexagonal head.

5. The apparatus of claim 1, wherein:
    the first orthopedic implement component driver is detachable from the first orthopedic implant component after installation of the first orthopedic implement component into to the orthopedic implant; and
    the second orthopedic implement component driver is detachable from the second orthopedic implant component after installation of the second orthopedic implement component into to the orthopedic implant.

6. The apparatus of claim 5, wherein:
    the first orthopedic implant is scored between the first orthopedic implant component and the first orthopedic implant component driver; and
    the second orthopedic implant formation is scored between the second orthopedic implant component and the second orthopedic implant component driver.

7. The apparatus of claim 6, wherein the first and second orthopedic implant formations are axially aligned.

8. The apparatus of claim 1, wherein the first and second orthopedic implant formations are coupled to one another.

9. An apparatus for installing orthopedic implant components onto an orthopedic implant, the apparatus comprising:
    a first orthopedic implant formation defining both a first orthopedic implant component and a first orthopedic implant component driver detachable from the first orthopedic implant component, the first orthopedic implant component driver having a transverse bore therein;
    a second orthopedic implant formation defining both a second orthopedic implant component and a second orthopedic implant component driver detachable from the second orthopedic implant, the second orthopedic implant component driver having an axially elongated bore therein; and
    a pin extending through the transverse bore of the first orthopedic implant component driver and the axially elongated bore of the second orthopedic implant component driver, and coupling the first and second orthopedic implant component drivers together;
    the first and second orthopedic implant formations configured for concerted installation of the first orthopedic implant component and the second orthopedic implant component onto an orthopedic implant and for removal of the first and second orthopedic implant component drivers from the respective first and second orthopedic implant by detachment therefrom.

10. The apparatus of claim 9, wherein:
    the first orthopedic implant component comprises a first spinal implant component;
    the second orthopedic implant component comprises a second spinal implant component; and
    the orthopedic implant is a spinal implant.

11. The apparatus of claim 10, wherein:
    the first spinal implant component comprises an end cap for a spinal rod holder;
    the second spinal implant component comprises a set screw for a spinal rod holder; and
    the spinal implant is a vertebral spinal rod bone screw assembly having a spinal rod holder.

12. The apparatus of claim 9, wherein:
    the first orthopedic implant component driver is a first hexagonal head; and
    the second orthopedic implant component driver is a second hexagonal head.

13. The apparatus of claim 9, wherein:
    the first orthopedic implant formation is scored between the first orthopedic implant component and the first orthopedic implant component driver; and
    the second orthopedic implant formation is scored between the second orthopedic implant component and the second orthopedic implant component driver.

14. The apparatus of claim 9, wherein the first and second orthopedic implant components are coupled to one another.

15. A method for installing orthopedic components onto an orthopedic implant, the method comprising:
- providing a first orthopedic implant formation that defines both a first orthopedic implant component and a first orthopedic implant component driver;
- providing a second orthopedic implant formation that defines both a second orthopedic implant component and a second orthopedic implant component driver, the second orthopedic implant formation situated onto the first orthopedic implant formation;
- placing the first and second orthopedic implant formations onto an orthopedic implant; and
- at least partially concertedly installing the first and second orthopedic implant components onto the orthopedic implant using the respective first and second orthopedic implant component drivers;
- wherein the first orthopedic implant is scored between the first orthopedic implant driver and the first orthopedic implant component, and the second orthopedic implant formation is scored between the second orthopedic implant driver and the second orthopedic implant component.

16. The method of claim 15, further comprising the steps of:
- detaching the first orthopedic implant driver from the first orthopedic implant component; and
- detaching the second orthopedic implant driver from the second orthopedic implant component.

17. The method of claim 16, wherein:
the first orthopedic implant driver is detachably connected to the first orthopedic implant component; and
the second orthopedic implant driver is detachably connected to the second orthopedic implant component.

18. The method of claim 15, wherein:
the first orthopedic implant component includes a spinal rod holder end cap; and
the second orthopedic implant component includes a spinal rod set screw.

19. The method of claim 15, wherein the first and second orthopedic implant component formations are coupled to one another.

\* \* \* \* \*